(12) United States Patent
Matityahu

(10) Patent No.: US 8,100,952 B2
(45) Date of Patent: Jan. 24, 2012

(54) DRUG DELIVERING BONE PLATE AND METHOD AND TARGETING DEVICE FOR USE THEREWITH

(75) Inventor: Amir M. Matityahu, Los Altos, CA (US)

(73) Assignee: Anthem Orthopaedics LLC, Los Altos, CA (US)

( * ) Notice: Subject to any disclaimer, the term of this patent is extended or adjusted under 35 U.S.C. 154(b) by 483 days.

(21) Appl. No.: 11/644,433

(22) Filed: Dec. 21, 2006

(65) Prior Publication Data

US 2007/0173843 A1 Jul. 26, 2007

Related U.S. Application Data

(60) Provisional application No. 60/753,182, filed on Dec. 22, 2005.

(51) Int. Cl.
*A61F 2/30* (2006.01)
(52) U.S. Cl. ........................................ 606/280; 606/281
(58) Field of Classification Search .................. 606/69, 606/70, 71, 72, 73, 280–299
See application file for complete search history.

(56) References Cited

U.S. PATENT DOCUMENTS

| | | | |
|---|---|---|---|
| 2,267,925 A | 2/1941 | Johnston | |
| 2,699,774 A | 1/1955 | Livingston | |
| 3,255,747 A | 6/1966 | Cochran et al. | |
| 3,463,148 A | 8/1969 | Treace | |
| 4,219,015 A * | 8/1980 | Steinemann | 606/280 |
| 4,297,993 A | 11/1981 | Harle | |
| 4,484,570 A | 11/1984 | Sutter et al. | |
| 5,057,111 A | 10/1991 | Park | |
| 5,108,399 A * | 4/1992 | Eitenmuller et al. | 606/77 |
| 5,190,544 A | 3/1993 | Chapman et al. | |
| 5,329,959 A | 7/1994 | Owen et al. | |
| 5,470,333 A | 11/1995 | Ray | |
| 5,545,164 A | 8/1996 | Howland | |

(Continued)

FOREIGN PATENT DOCUMENTS

DE 10131992 B4 11/2006

(Continued)

OTHER PUBLICATIONS

Apr. 6, 2009 Non-Final Rejection issued by the U.S. Patent Office for corresponding patent U.S. Appl. No. 11/588,037; pp. 1-16.

(Continued)

*Primary Examiner* — Thomas C. Barrett
*Assistant Examiner* — Christopher Beccia
(74) *Attorney, Agent, or Firm* — Dorsey & Whitney LLP

(57) ABSTRACT

An implantable bone plate for use with a plurality of attachment screws for treating a fracture of a bone in a mammalian body is provided. The implantable bone plate includes an elongate body extending along a longitudinal axis and having substantially parallel outer and inner surfaces. A plurality of holes is spaced longitudinally along the elongate body and extended between the first and second surfaces. The plurality of holes is adapted to receive the plurality of attachment screws. The inner surface of the elongate body is provided with at least one recess for receiving an eluting material that treats the mammalian body after implantation of the elongate body in the mammalian body. Additionally, the elongate body is provided with at least one access hole extending through the outer surface to the at least one recess for permitting introduction of the eluting material into the at least one recess.

12 Claims, 5 Drawing Sheets

U.S. PATENT DOCUMENTS

| | | | |
|---|---|---|---|
| 5,545,165 | A | 8/1996 | Biedermann et al. |
| 5,603,713 | A | 2/1997 | Aust et al. |
| 5,616,144 | A * | 4/1997 | Yapp et al. .................... 606/280 |
| 5,735,853 | A | 4/1998 | Olerud |
| 5,897,557 | A | 4/1999 | Chin et al. |
| 5,954,722 | A | 9/1999 | Bono |
| 6,214,012 | B1 * | 4/2001 | Karpman et al. ............... 606/93 |
| 6,235,033 | B1 | 5/2001 | Brace et al. |
| 6,293,949 | B1 | 9/2001 | Justis et al. |
| 6,331,179 | B1 | 12/2001 | Freid et al. |
| 6,342,055 | B1 | 1/2002 | Eisermann et al. |
| 6,544,266 | B1 * | 4/2003 | Roger et al. .................... 606/70 |
| 6,575,975 | B2 | 6/2003 | Brace et al. |
| 6,663,632 | B1 | 12/2003 | Frigg |
| 6,783,382 | B2 | 8/2004 | Felps |
| 6,786,909 | B1 | 9/2004 | Dransfeld et al. |
| 6,890,334 | B2 | 5/2005 | Brace et al. |
| 6,893,443 | B2 | 5/2005 | Frigg et al. |
| 6,908,466 | B1 | 6/2005 | Bonutti et al. |
| 6,916,321 | B2 | 7/2005 | Tenhuisen et al. |
| 6,916,483 | B2 | 7/2005 | Ralph et al. |
| 7,195,633 | B2 | 3/2007 | Medoff et al. |
| 7,547,305 | B2 | 6/2009 | Rapp |
| 2002/0058939 | A1 | 5/2002 | Wagner et al. |
| 2002/0065517 | A1 | 5/2002 | Paul |
| 2002/0077630 | A1 | 6/2002 | Lin |
| 2002/0111630 | A1 | 8/2002 | Ralph et al. |
| 2003/0105461 | A1 * | 6/2003 | Putnam ........................... 606/69 |
| 2003/0105471 | A1 | 6/2003 | Schlapfer et al. |
| 2003/0199876 | A1 | 10/2003 | Brace et al. |
| 2004/0013703 | A1 | 1/2004 | Ralph et al. |
| 2004/0015169 | A1 * | 1/2004 | Gause ............................. 606/63 |
| 2004/0039387 | A1 | 2/2004 | Gause et al. |
| 2004/0059335 | A1 | 3/2004 | Weaver et al. |
| 2004/0068319 | A1 | 4/2004 | Cordaro |
| 2004/0116931 | A1 | 6/2004 | Carlson |
| 2004/0127896 | A1 | 7/2004 | Lombardo et al. |
| 2004/0127904 | A1 | 7/2004 | Konieczynski et al. |
| 2004/0167522 | A1 * | 8/2004 | Niederberger et al. ......... 606/69 |
| 2004/0181228 | A1 | 9/2004 | Wagner et al. |
| 2004/0204712 | A1 | 10/2004 | Kolb et al. |
| 2004/0204713 | A1 | 10/2004 | Abdou |
| 2004/0220570 | A1 | 11/2004 | Frigg |
| 2004/0236332 | A1 | 11/2004 | Frigg |
| 2004/0254579 | A1 | 12/2004 | Buhren et al. |
| 2005/0010226 | A1 | 1/2005 | Grady, Jr. et al. |
| 2005/0015131 | A1 | 1/2005 | Fourcault et al. |
| 2005/0043736 | A1 | 2/2005 | Mathieu et al. |
| 2005/0049594 | A1 | 3/2005 | Wack et al. |
| 2005/0070904 | A1 | 3/2005 | Gerlach et al. |
| 2005/0080421 | A1 | 4/2005 | Weaver et al. |
| 2005/0107796 | A1 | 5/2005 | Gerlach et al. |
| 2005/0124994 | A1 | 6/2005 | Berger et al. |
| 2005/0149027 | A1 | 7/2005 | Campbell et al. |
| 2005/0154392 | A1 | 7/2005 | Medoff et al. |
| 2005/0159753 | A1 * | 7/2005 | Kitchens ......................... 606/80 |
| 2005/0165400 | A1 | 7/2005 | Fernandez |
| 2005/0192576 | A1 | 9/2005 | Michelson |
| 2005/0246021 | A1 | 11/2005 | Ringeisen et al. |
| 2006/0058798 | A1 | 3/2006 | Roman et al. |
| 2006/0149263 | A1 | 7/2006 | Newcomb et al. |
| 2006/0200134 | A1 | 9/2006 | Freid et al. |
| 2006/0235399 | A1 | 10/2006 | Carls et al. |
| 2006/0235405 | A1 | 10/2006 | Hawkes |
| 2007/0027230 | A1 * | 2/2007 | Beyar et al. .................... 523/117 |
| 2007/0055257 | A1 * | 3/2007 | Vaccaro et al. ................. 606/73 |
| 2007/0088362 | A1 * | 4/2007 | Bonutti et al. .................. 606/99 |
| 2007/0162016 | A1 | 7/2007 | Matityahu |
| 2007/0173843 | A1 | 7/2007 | Matityahu |
| 2008/0300637 | A1 | 12/2008 | Austin et al. |
| 2008/0360550 | | 12/2008 | Matityahu |

FOREIGN PATENT DOCUMENTS

| | | |
|---|---|---|
| WO | WO-2004/084701 | 10/2004 |
| WO | 2007/050796 | 5/2007 |

OTHER PUBLICATIONS

Jul. 2, 2009 Amendment to Apr. 6, 2009 Non-Final Rejection for corresponding U.S. Appl. No. 11/588,037; pp. 1-15.

Nov. 13, 2009 Non-Final Rejection issued by the U.S. Patent Office for corresponding patent U.S. Appl. No. 11/588,037; pp. 1-16.

Mar. 2, 2010 Amendment to Nov. 13, 2009 Non-Final Rejection for corresponding U.S. Appl. No. 11/588,037; pp. 1-13.

Jun. 24, 2010 Non-Final Rejection issued by the U.S. Patent Office for corresponding patent U.S. Appl. No. 11/588,037; pp. 1-17.

Oct. 25, 2010 Amendment to Jun. 24, 2010 Non-Final Rejection for corresponding U.S. Appl. No. 11/588,037; pp. 1-18.

Jan. 3, 2011 Final Rejection issued by the U.S. Patent Office for corresponding patent U.S. Appl. No. 11/588,037; pp. 1-15.

Feb. 23, 2011 Amendment to Jan. 3, 2011 Final Rejection issued by U.S. Patent Office for patent U.S. Appl. No. 11/588,037; pp. 1-5.

Mar. 4, 2011 Notice of Allowance issued by the U.S. Patent Office for corresponding patent U.S. Appl. No. 11/588,037; pp. 1-6.

Sep. 18, 2009 Non-Final Rejection issued by the U.S. Patent Office for corresponding patent U.S. Appl. No. 11/759,429; pp. 1-19.

Mar. 18, 2010 Amendment to Sep. 18, 2009 Non-Final Rejection for corresponding U.S. Appl. No. 11/759,429; pp. 1-11.

Jul. 9, 2010 Final Rejection issued by the U.S. Patent Office for corresponding patent U.S. Appl. No. 11/759,429; pp. 1-15.

Oct. 25, 2010 Amendment After Final to Jul. 9, 2010 Final Rejection for corresponding U.S. Appl. No. 11/759,429; pp. 1-14.

Translation of Sep. 4, 2009 Official Action issued by the Chinese Patent Office for corresponding CN patent application No. 200680039692.4, pp. 1-17.

Mar. 3, 2010 Instructional letter in response to Sep. 4, 2009 Official Action for corresponding CN patent application No. 200680039692.4, pp. 1-11.

Translation of Sep. 20, 2010 Official Action issued by the Chinese Patent Office for corresponding CN patent application No. 200680039692.4, pp. 1-10.

Oct. 19, 2010 Instructional letter in response to Sep. 20, 2010 Official Action for corresponding CN patent application No. 200680039692.4, pp. 1-5.

Translation of Jan. 22, 2010 Official Action issued by Chinese Patent Office for corresponding CN patent application No. 20068005257.8, pp. 1-9.

Apr. 29, 2008 International Preliminary Report on Patentability issued by the International Bureau of WIPO for corresponding PCT patent application serial No. PCT/US2006/041850, pp. 1-5.

Jun. 24, 2008 International Preliminary Report on Patentability issued by the International Bureau of WIPO for corresponding PCT application serial No. PCT/US2006/062577, pp. 1-5.

Dec. 7, 2009 International Preliminary Report on Patentability issued by the International Bureau of WIPO Office for corresponding patent application serial No. PCT/US2008/055338, pp. 1-7.

Mar. 28, 2011 Supplementary European Search Report issued by the European Patent Office for patent application serial No. EP 06840346.8, pp. 1-5.

Jun. 29, 2011 Supplementary European Search Report issued by the European Patent Office for corresponding patent application serial No. EP 06817405.1, pp. 1-8.

* cited by examiner

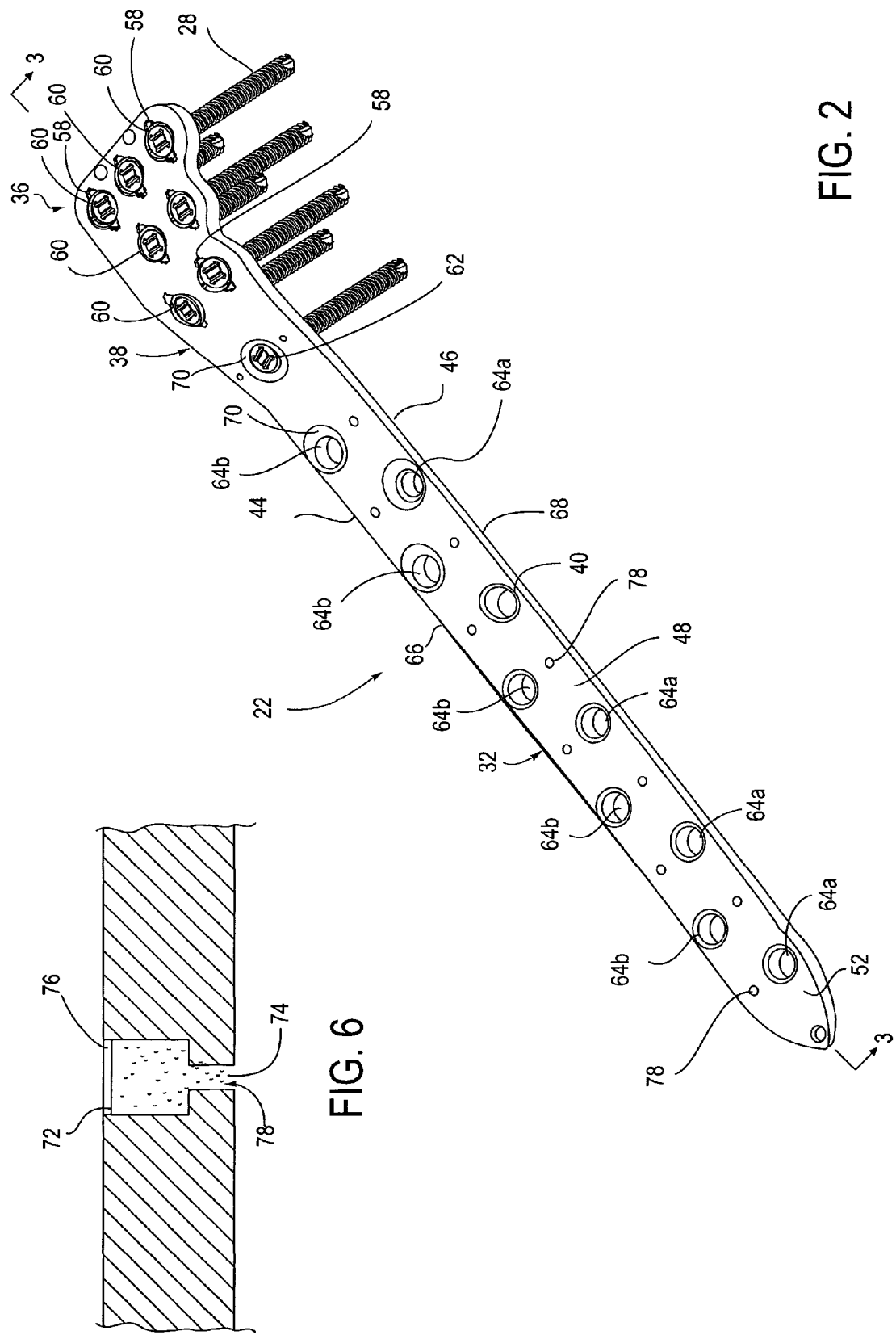

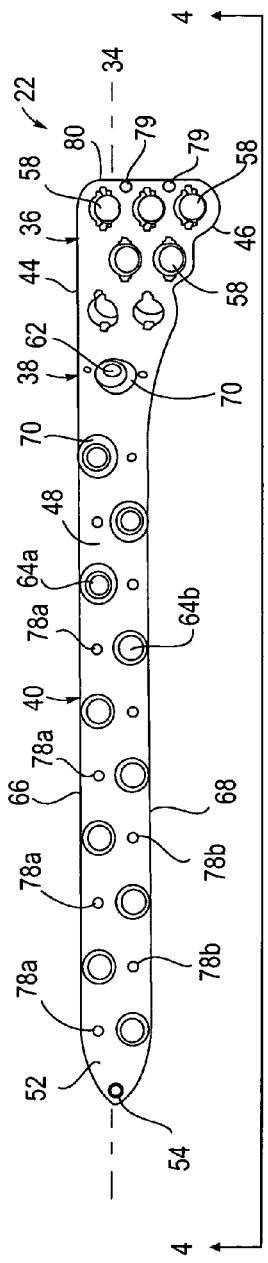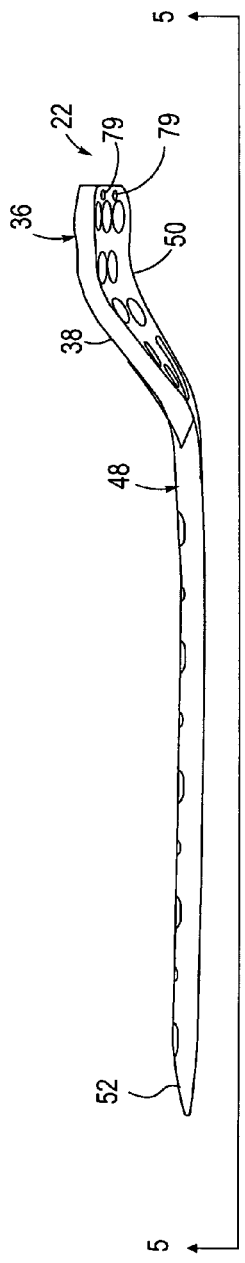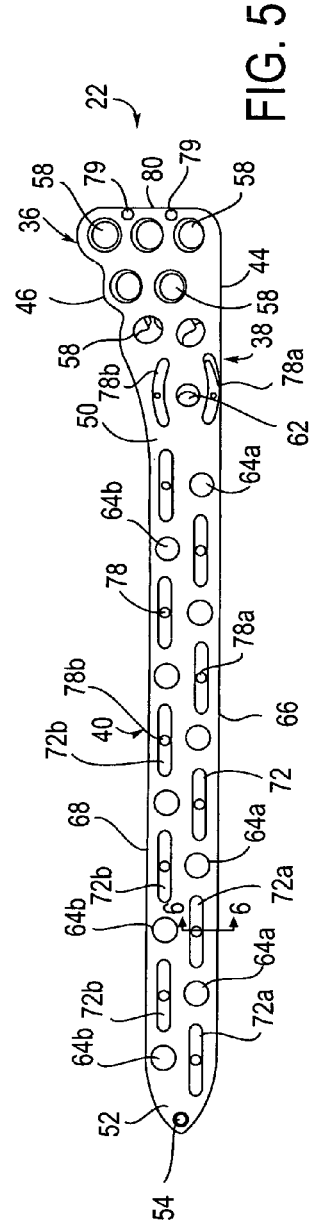

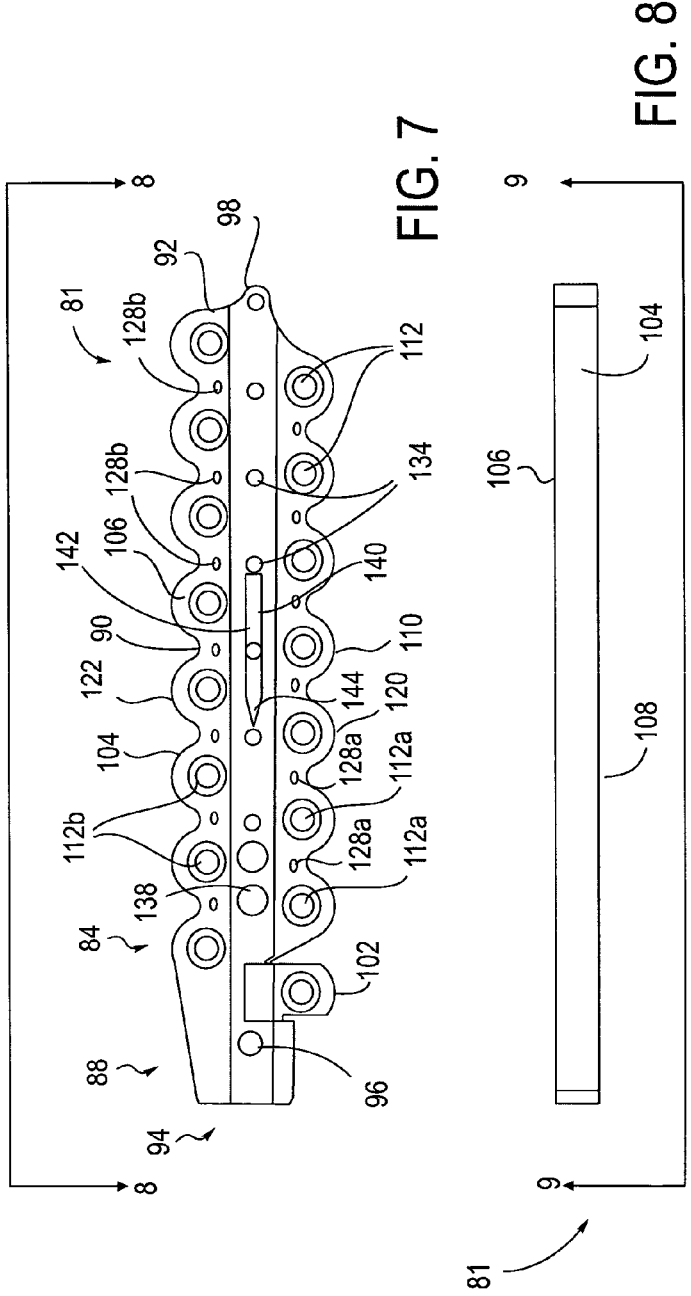
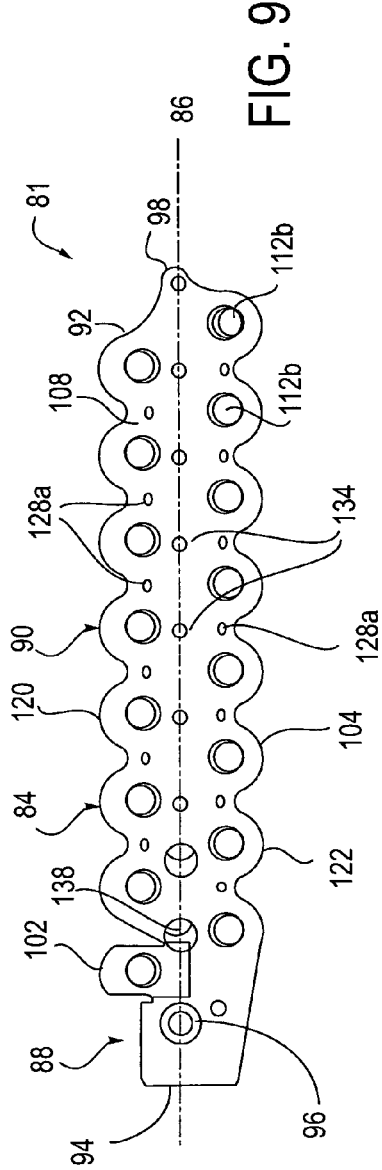

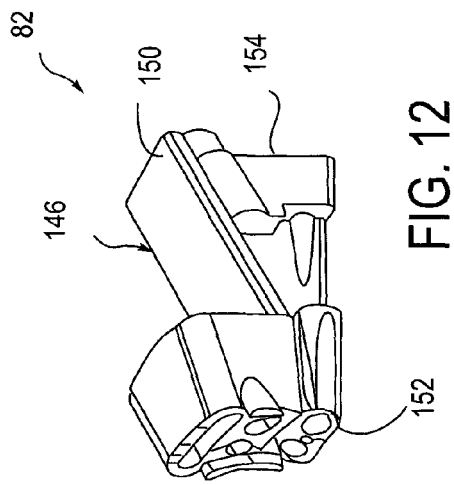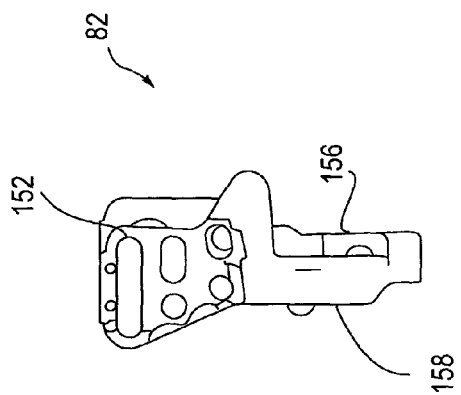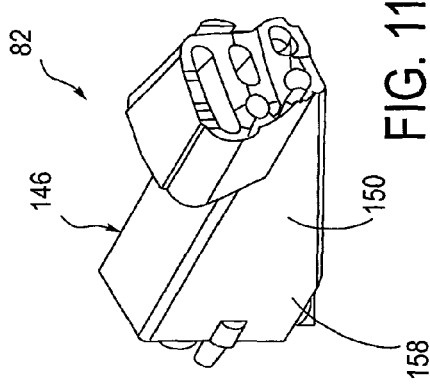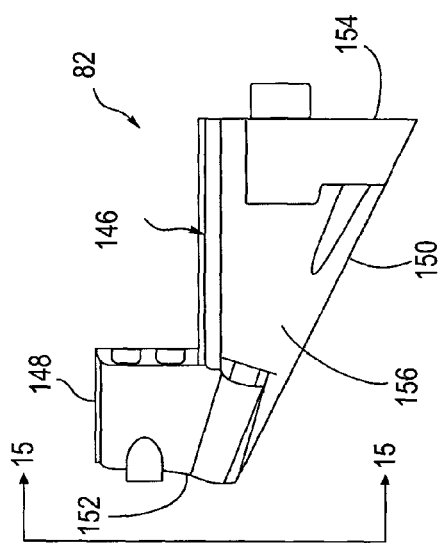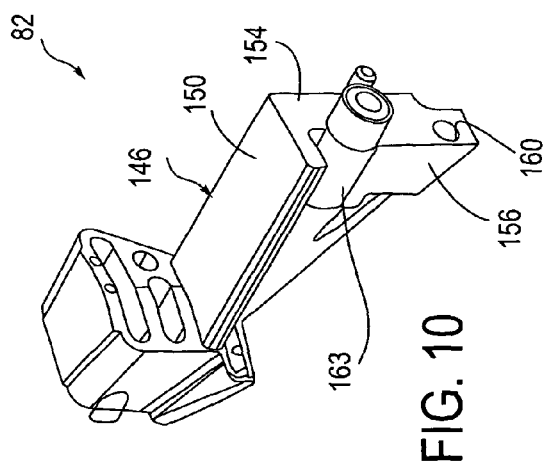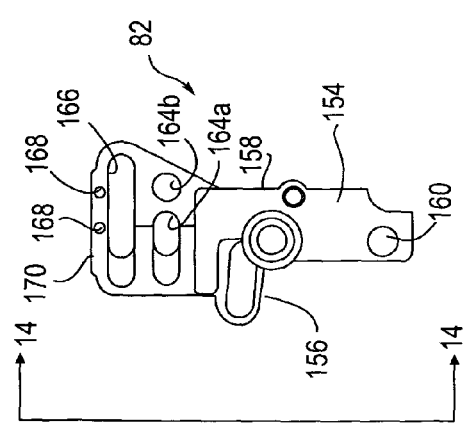

DRUG DELIVERING BONE PLATE AND METHOD AND TARGETING DEVICE FOR USE THEREWITH

CROSS-REFERENCE TO RELATED APPLICATIONS

This application is a non-provisional application that claims priority to U.S. Provisional Application Ser. No. 60/753,182 filed on Dec. 22, 2005, the entire content of which is incorporated herein by this reference.

FIELD

The present invention relates to a bone plate for use with a mammalian body, and more particularly a bone plate having a medicament therein.

BACKGROUND

The skeletal system includes many long and flat bones. which, for example with respect to a human body, extend from the human torso. These bones include the pelvis, spine, humerus, radius, ulna, bones of the hand, femur, tibia, fibula, and bones of the foot. These bones are particularly exposed to trauma from accidents, which can cause complex fractures of the bones.

Bone plates and bone screws are common mechanical devices used to reattach fractured bones. The bone plates are usually placed longitudinally along the periphery of the long bone and have holes or openings through which screws may be inserted into the long bone transversely.

Once the bone plate is in place, however, it is often difficult to administer medication to the fractured site of the bone. In order to deliver medication to the bone, a large incision is sometimes made in the patient, such as near the bone, for accessing the whole fracture site. This may cause needless complications at the fractured site. Therefore, there is a need for an apparatus and method for treating a fracture site of a bone in a mammalian body without removing the bone plate.

SUMMARY

An implantable bone plate for use with a plurality of attachment screws for treating a fracture of a bone in a mammalian body is provided. The implantable bone plate includes an elongate body extending along a longitudinal axis and having substantially parallel outer and inner surfaces. A plurality of holes is spaced longitudinally along the elongate body and extend between the first and second surfaces. The plurality of holes is adapted to receive the plurality of attachment screws. The inner surface of the elongate body is provided with at least one recess for receiving an eluting material that treats the mammalian body after implantation of the elongate body in the mammalian body. Additionally, the elongate body can be provided with at least one access hole extending through the outer surface to the at least one recess for permitting introduction of the eluting material into the at least one recess.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 2 is a top perspective view of the bone plate of FIG. 1.

FIG. 3 is a top plan view of the bone plate of FIG. 1 taken along the line 3-3 of FIG. 2.

FIG. 4 is a posterior side elevational view of the bone plate of FIG. 1 taken along the line 4-4 of FIG. 3.

FIG. 5 is a bottom plan view of the bone plate of FIG. 1 taken along the line 5-5 of FIG. 4.

FIG. 6 is a cross-sectional view of the bone plate of FIG. 1 taken along the line 6-6 of FIG. 5.

FIG. 7 is a top plan view of an upper portion of the targeting device of FIG. 1.

FIG. 8 is a posterior side view of the upper portion of the targeting device of FIG. 1 taken along the line 8-8 of FIG. 7.

FIG. 9 is a bottom plan view of the upper portion of the targeting device of FIG. 1 taken along the line 9-9 of FIG. 8.

FIG. 10 is a top anterior perspective view of a lower portion of the targeting device of FIG. 1.

FIG. 11 is a bottom posterior perspective view of the lower portion of the targeting device of FIG. 1.

FIG. 12 is a bottom anterior perspective view of the lower portion of the targeting device of FIG. 1.

FIG. 13 is a top plan view of the lower portion of the targeting device of FIG. 1 taken along the line 13-13 of FIG. 12.

FIG. 14 is an anterior side elevational view of the lower portion of the targeting device of FIG. 1 taken along the line 14-14 of FIG. 13.

FIG. 15 is a bottom plan view of the lower portion of the targeting device of FIG. 1 taken along the line 15-15 of FIG. 14.

DETAILED DESCRIPTION OF THE VARIOUS EMBODIMENTS

Figure 1:
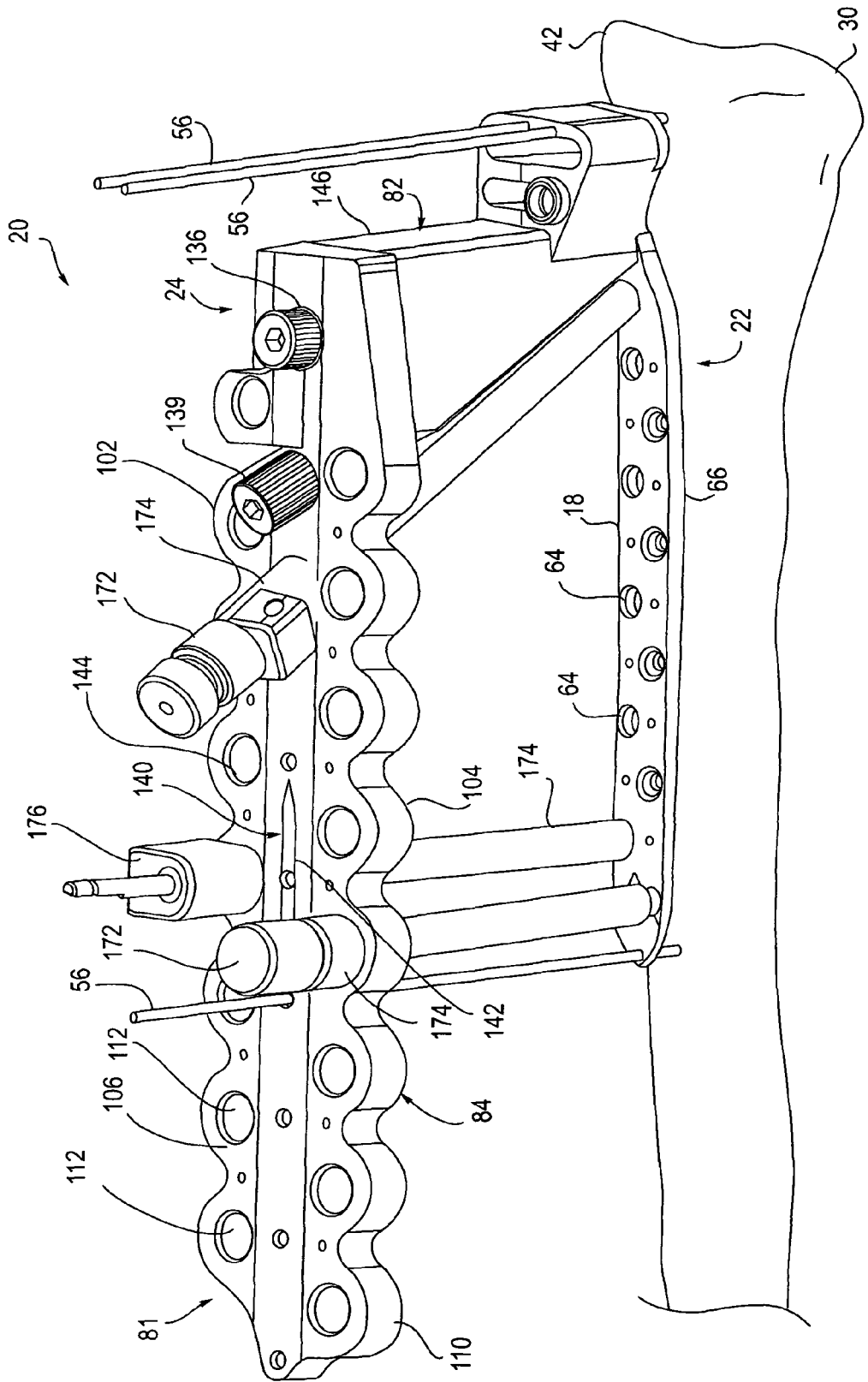
FIG. 1 is a top, posterior perspective view of a drug delivering bone plate of the present invention with a targeting device of the present invention mounted thereto.

In general, the present invention relates to a bone-fastening system 20 that includes a bone locking plate or bone plate 22, a targeting device 24 for aligning the bone locking plate 22 in position with a mammalian body and a plurality of bone or attachment screws 28 for attachment of the bone plate 22 to the mammalian body, as shown in FIG. 1. The bone locking plate 22 is configured to deliver a therapeutic medication or drug to a bone to which the plate 22 is attached. More specifically, the bone locking plate 22 can include the drug at the time of attachment of the plate 22 to the bone, or the drug can be delivered to the plate 22 after attachment to the bone. The targeting device 24 can aid in delivering the drug through the bone plate 22 after attachment of the bone plate to the bone. Although the bone fastening assembly can be used with any suitable bone of a mammalian body, for example, a long bone such as the humerus, radius, ulna, femur or fibula, the bone fastening assembly 20 is described and illustrated herein for use with a tibia 30 and specifically the proximal lateral tibia.

The bone plate 22 is formed from an elongate body 32 made from any suitable material, such as a composite material, resorbable material or metal, and is preferably made from stainless steel or titanium. The elongate body 32 extends along a longitudinal centerline 32 and forms with a head 36, a neck 38, and a shaft 40 (see FIGS. 1-5). The head 36 of the bone plate 22 is anatomically contoured to an end of a long bone being treated, in this instance, an end 42 of the tibia 30. The shaft and the neck, located between the head 36 and the shaft 40, are also anatomically shaped relative to the tibia 30. The elongate body 32 has an anterior or front 44 and a posterior or back 46, shown most clearly in FIG. 4, and an outer surface or face 48 and an inner or bone-facing surface 50 extending between the anterior 44 and the posterior 46, as shown best in FIGS. 3 and 5. A tapered distal end 52 extends from the shaft 40.

The bone plate 22 is provided with a least one aperture or hole 58 for directly or indirectly receiving bone screws 28. In this regard, the hole 58 may be configured to receive a bushing 60 to indirectly receive a bone or attachment screw 28, and the hole 58 can be threaded to directly receive the bone screw 28 (see FIG. 2). The combination of the threaded portion and the bushing 60 may be configured to allow the bushing to pivot about any one axis, for example, an axis extending in the plane of the bone plate 22. It is appreciated that any combination of threaded and bushing-receiving hole can be provided. For example, the combination of thread and bushing-receiving holes may be similar to those disclosed in U.S. Non-provisional application Ser. No. 11/588,037, filed Oct. 25, 2006, the entire content of which is incorporated herein by this reference. In the illustrated tibia bone plate 22, the at least one aperture 58 is a plurality of holes or apertures 58 that is provided within the head 36 of the elongate body 32.

The bone plate 22 also includes at least one threaded aperture or hole 62 that is provided within the neck 38, and a plurality of threaded apertures or holes 64 that is provided within the shaft 40 of the body 32. Each of the thread holes may be configured to receive the attachment screw 28. The threaded holes 64 in the shaft 40 can be arranged in any suitable configuration or array. In one embodiment, the shaft 40 is provided with a first plurality of holes 64a that is longitudinally spaced apart along a first side 66 of the centerline 34 and a second plurality of holes 64b that are longitudinally spaced apart along a second side 68 of the centerline 34 (see FIGS. 2 and 3). As such, the first plurality of holes 64a is longitudinally offset relative to the second plurality of holes 64b. Additionally, holes 64a are interspersed at approximate equal longitudinal distances from each other along the length of the shaft 40. Likewise, holes 64b are interspersed at approximate equal longitudinal distances from each other along the length of the shaft 40. Each of the holes 62 and 64 is preferably threaded in a direction inclined toward the centerline of the shaft 40. More preferably, the bone plate 22 apertures in the shaft 40 have concavity away from the bone 30 being treated, more specifically, the apertures 64 are tapered inwardly from the outer face 48 to the inner face 50 of the bone plate 22, as shown most clearly in FIG. 2. The angle of inclination, shown in FIG. 2, can range from 3 to 15 degrees and preferably approximately 6 degrees.

Each of the holes 62 and 64 is preferably formed with an angular or tapered surface 70 which ramps inwardly from the outer surface 48 toward a centerline of the hole, as shown in FIG. 3. This urges the leading end of a screw toward the center of the bore during placement of the screw in a body of a patient. When the outer surface 48 of the shaft 40 is viewed in plan, as shown in FIG. 3, the entrance or ramped surface 70 of at least some of holes 64 is oblong shaped or oval shaped relative to the centerline of the corresponding hole. Likewise, the entrance or ramped surface 70 of the hole 62 may have an oblong shape or oval shape relative to the centerline of the corresponding hole. The long dimension of such oblong-shaped ramps is preferably aligned with, or parallel, to the longitudinal centerline 34 of the shaft 40. The number and location of screw holes 62 and 64 having an oblong-shaped or oval-shaped ramped surface can vary.

As best shown in FIG. 5, the elongate body 32 of the bone plate 22 is provided with at least one recess, slit, slot, or groove 72 on the inner surface 50 for receiving an eluting material 74 that contains the drug, medication, or other therapeutic or prophylactic agents to be delivered by the bone plate 22. The inner face or surface 50 of the plate 22 is configured to face the bone 30 being treated, and is preferably provided with a plurality of such recesses, slits, slots, or grooves 72 formed in the underside 50 of the plate 22.

In one embodiment, the recesses 72 are longitudinally-extending grooves spaced between adjacent screw holes 62 and 64 of the bone plate 22. More specifically, the inner surface 50 of the plate 22 provides a first plurality of recesses 72a longitudinally aligned and spaced apart along the first side 66 of the centerline 34 of the bone plate 22. A second plurality of recesses 72b is also provided along the inner surface 50 and are longitudinally aligned and spaced apart along the second side 68 of the centerline 34 of the bone plate 22. The first plurality of recesses 72a is preferably offset relative to the second plurality of recesses 72b, such that each recess 72 is aligned opposite at least one screw hole 64. Such a recess and screw hole arrangement, particularly when the recesses 72 are aligned longitudinally relative to the longitudinal axis 34 of the bone plate 22, provides for a strong bone plate because it increases the transverse cross-section of the device having material that provides strength to the bone plate 22. Accordingly, the bone plate 22 is less likely to snap or break due to bending or torque about a transverse axis that is perpendicular to the longitudinal axis 34 of the bone plate 22. Although the recesses 72 are shown and described as longitudinally extending grooves, it is appreciated that these recesses 72 can be of any other suitable size and configuration. For example, the recesses 72 may be transversely aligned or at any angle relative to the longitudinal centerline 34 of the plate 22.

In one embodiment, the bone plate 22 includes at least one access bore or port 78 that is provided on the outer surface 48 and extends through the bone plate 22 to communicate with the at least one related recess 72. The access port 78 allows a user to insert the eluting material 74 into a related recess 72, after the bone plate 22 has been attached to the bone 30. As illustrated in FIGS. 1 thru 3, the bone plate 22 preferably includes a plurality of access ports 78 spaced apart and configured in a pattern that corresponds with the pattern of recesses located on the inner surface 50 of the bone plate 22. The plurality of ports 78 allow the eluting material 74 to be delivered to each of the recesses 72 by a respective access port 78 provided on the outer surface 48 of the bone plate 22 that extends to the related recess 72. Like their corresponding recesses 72, the access ports 78 are spaced between adjacent screw holes 62 and 64 on the neck 38 and the shaft 38. At least one of the access ports 78 is aligned opposite at least one of the screw holes 62 and 64. This arrangement is such that a first plurality of access ports 78a is aligned longitudinally with the longitudinal axis 34 on the first side 66 of the bone plate 22, and a second plurality of access ports 78b are aligned longitudinally with the longitudinal axis 34 on the second side 68 of the bone plate 22.

In one embodiment, at least one recess 72 on the inner surface of the plate 22 is covered by a biodegradable film or biofilm 76 that forms a closed cavity, as best shown in FIG. 6. The biofilm 76 may include the eluting material 74 that is slowly released over time. The biofilm 76 allows for a graded release time of the eluting material 74 within the cavity, such release time being a function of the material properties of the biofilm 76. Alternatively, the biofilm 76 and the eluting material 74 can be the same material.

More specifically, the rate of release of the therapeutic agent from the biofilm generally depends on the concentration of the therapeutic agent in the composition and the choice of biofilm. For a particular biofilm, the rate of release may further be controlled by the inclusion of one or more additives that function as a release rate modification agent, and by varying the concentration of that additive. This release rate modification additive may be, for example, an organic substance, which is water soluble or water insoluble, or a substance that is degraded by controlled enzymatic actions of the body. Useful release rate modification agents include, for example, fatty acids, triglycerides, organic solvents, plasticizing compounds, polysaccharides, glycolides, lactides, and polyethylene glycol.

The bone plate 22 includes at least one guide and alignment hole 79. The guide and alignment hole 79 receives a guide wire or rod 56 to align the bone plate 22 along the bone 30. As illustrated, the head 36 of the bone plate 22 includes two guide and alignment holes 79 near a peripheral edge 80 of the head; the distal end 52 of the bone plate also includes at least one guide and alignment bore 79 along the centerline 34 of the bone plate.

In one embodiment, shown in FIG. 1, the targeting device 24 has a plate-like upper portion that may be termed a plate, targeting jig, plate handle or targeting arm 81, and an upstanding lower portion that may be termed a block or base 82. The targeting arm 81 can be constructed of any suitable material such as a composite material, carbon fiber, plastic or metal and preferably carbon fiber. Such material is preferably radio-opaque or radiolucent. The base 82 can be constructed of any suitable material such as a radio-opaque, radiolucent or radio-dense material such as composite material, carbon fiber plastic, or metal, and preferably aluminum, stainless steal or titanium.

The targeting arm 81 is formed from an elongate body 84 extending along a longitudinal axis 86. The elongated body 84 includes a proximal portion or head 88, a central portion or stem 90, and a distal portion or tail 92, shown in FIGS. 1 and 7-9. The stem 90 is located between the head 88 and the tail 92. The head 88 has a proximal end 94. The head 88 further includes a threaded bore 96 that is used to couple the targeting arm 81 to the base 82. The tail end 92 has a distal end or tip 52.

The elongated body 84 further includes an anterior or front side 102 and a posterior or back side 104, shown clearly in FIG. 1, and an outer surface or face 106 and an interior or bone-plate facing surface 108 extending between the anterior side 102 and the posterior side 104. The anterior side 102 and the posterior side 104 may be configured to include a plurality of curvatures or serrations 110 that allow a user to easily handle and grasp the targeting device 24 and decreases the weight of the targeting device for easier manipulation.

The elongated body 84 is provided with at least one alignment bore 112, preferably threaded for aligning a variety of tools with a respective screw hole of the holes 62 and 64 in the bone plate 22. As illustrated, the targeting arm 81 includes a plurality of alignment bores 112 that may receive various tools, such as a drill guide 114 or a trocar 116 as shown in FIG. 1. The alignment bores 112 are provided in the stem 90 and can be arranged in any suitable manner corresponding to the screw holes 62 and 64 of the bone plate 22. In one embodiment, the targeting arm 81 is provided with a first plurality of alignment bores 112a longitudinally spaced apart along a first side 120 of the longitudinal centerline 86 of the targeting arm 81, and a second plurality of alignment bores 112b longitudinally spaced apart along a second side 122 of the centerline 86. As such, the first plurality of alignment bores 112a is offset relative to the second plurality of alignment bores 112b in the same manner that the screw holes 64 are offset to one another. More preferably, bores 112a are interspersed at approximate equal longitudinal distances from each other along a length of the stem 90; likewise, bores 112b are interspersed at approximate equal longitudinal distances from each other along the length of the stem 90. It is appreciated that a targeting device 24 and bone plate 22 having any suitable arrangement of bores can be provided. For example, a plate design that fits a mammalian bone and having any suitable arrangement of bores, and a corresponding targeting device having any corresponding or other arrangement of bores, can be provided to allow for percutaneous insertion of screws for fixation of the bone plate to a bone.

The targeting arm or handle 81 of the targeting device 24 further includes at least one guide hole 128 for aligning a needle (not shown) to a corresponding access port 78. The needle includes the eluting material or materials 74 that can be injected through the access port 78 and into a related recess 72. As clearly illustrated in FIGS. 7 and 9, the targeting arm 81 includes a plurality of guide holes 128. The plurality of guide holes 128 are spaced apart and configured in a pattern that corresponds with the pattern of access ports 78 in the bone plate 22. More specifically, a first plurality of guide holes 128a are spaced between adjacent alignment bores 112 of the first plurality of alignment bores 112a along the first side 120 of the centerline 86. Likewise, a second plurality of guide holes 128b are spaced between adjacent alignment bores 112 of the second plurality of alignment bores 112b on the second side 122 of the centerline 86 of the targeting device 24. The first plurality of guide holes 128a are offset relative to the second plurality of guide holes 128b, such that each guide hole 128 is aligned opposite at least one of the alignment bores 112. As such, a guide hole and alignment bore arrangement is aligned longitudinally with the longitudinal axis of the targeting device 24 in the same manner that the access ports in the bone plate 22 are longitudinally aligned and spaced apart from each other. More preferably, the guide holes 128a are interspersed at approximate equal longitudinal distances from each other along the length of the stem 90; likewise, the guide holes 128b are interspersed at approximate equal longitudinal distances from each other along the length of the stem 90.

The targeting arm 81 of the targeting device 24 includes at least one guide and alignment bore 134 along a portion of the centerline 86. The guide wire 54 extends through the guide and alignment bore 134 and the corresponding guide and alignment bore 79 provided in the bone plate. This coupling action allows the targeting device to properly align the bone plate to the bone. As shown in FIGS. 1 and 7, the targeting arm 81 preferably includes a plurality of guide and alignment bores 134 provided along a portion of the centerline 86 of the stem 90. At least one of these guide and alignment bores is used to align the distal end 98 of the targeting device 24 to the distal end 52 of the bone plate 22. Additionally, by using multiple guide and alignment bores 134 along the centerline 86, the targeting arm 81 can be used along with any bone plate of various lengths.

The targeting arm 81 also includes at least one rearward threaded bore 138 near or about the proximal end 94 of the head 88 and along the centerline 86. In the illustrated example, the targeting arm 81 includes two rearward threaded bores 138. At least one of the rearward thread bores 138 receives an additional attachment screw 28 for securing the targeting device 24 to the head of the bone plate 22, as clearly shown in FIG. 1. Additionally, at least one of the rearward thread bores 138 may be used to align various tools with the bone 30 via the bone plate 22.

Each of the bores and/or holes 112, 138, of the targeting arm 81, are preferably formed with an angular or tapered surface which ramps inwardly from the outer surface toward the centerline of the hole as shown in FIG. 7. This angular surface allows the leading end of various tools and screws to lean toward the center of the bore to aid in the placement of the screw 28 in a body of a patient. When the outer surface 106 of the stem 90 is viewed in plan, the entrance or ramped surface of at least some of the holes or bores is oblong shaped or oval shaped relative to the centerline of the corresponding hole. The long dimension of such oblong-shaped ramps is preferably aligned with, or parallel to, the longitudinal centerline of the stem. The number and location of bores and/or holes having an oblong-shaped or oval-shaped ramped surface can vary.

On the outer surface 106 of the upper portion 80, an alignment recess 140 may also be positioned along the centerline 86 (See FIGS. 1 and 7). The alignment recess 140 is an arrow having a linear portion 142 extending from a wedge-shaped end 144; the wedge-shaped end 144 is pointed toward the distal end 98 of the targeting arm 81. Since the targeting arm 81 of the targeting device 24 is coupled in parallel to the bone plate, the centerline 86 of the targeting device 24 is parallel to the centerline 34 of the bone plate 22. This allows the user the ability to use the alignment recess 140, under fluoroscopy, to properly align the centerline 34 of the bone plate 22 to the fractured site of the bone 30. In other words, when the alignment recess 140 is centered properly over the bone 30, the bone plate 22 is also centered properly over the bone.

The base 82 of the targeting device 24 is formed of a vertically extending body 146 having a base portion 148 and an upright or upstanding portion 150, as clearly shown in FIG. 1. The extending body 146 has a bottom or bone-plate facing surface 152 and an upper or upper portion facing surface 154, and an anterior or front side 156 and a posterior or back side 158 extending between the bottom surface 152 and the upper surface 154 (See FIGS. 10-15). The bottom surface 152 of the base portion 148 is contoured to communicate with the head 36 of the bone plate 22. Likewise, the upper surface 154 of the upright portion 150 is contoured to communicate with the interior surface 108 of the head 88 of the targeting arm 81.

As best shown in FIG. 10, the upright portion 150 of the base 82 includes at least one rearward bore 160 positioned on the upper surface 154. The rearward bore 160 corresponds to at least one rearward bore 138 of the upper portion 80 for receiving the additional attachment screw 139 for securing the targeting device 24 to the head 36 of the bone plate 22. All of such attachment screws, similar to the attachment screw 139, are decoupled from the bone plate 22 after insertion and attachment of the bone plate 22 to the bone 30 of the patient.

The upright portion 150 further includes an attachment screw 162 and a threaded orifice 163 that receives the attachment screw 162. The attachment screw 162 is extended through the threaded bore 96 of the head 88 of the targeting arm 81 and tightened to secure the targeting arm 81 to the base 82.

As best shown in FIG. 13, the base 82 includes at least one forward bore 164 for attaching the targeting device 24 to the head 36 of the bone plate 22. For example, the base portion 148 includes a plurality of forward bores 164 used to attach the targeting device 24 to the head 36 of the bone plate 22 by one or more screws 28 or other fasteners which screw into respective one or more screw holes provided in the head 36 of the bone plate 22. At least one of the forward bores 164 may include a single forward bore 164*a* that provides access to multiple screw holes that are aligned beneath this forward bore; additionally, at least one forward bore 164*b* provides access to a single corresponding screw hole of the bone plate 22 that is beneath this forward bore.

The base portion 148 further includes a longitudinal extending bore 166 that provides access to multiple screw holes 58 in the head 36 of the bone plate 22. Additionally, the base portion 148 may include at least one guide and alignment bore 168 to align the targeting device 24 to the bone plate 22. For example, the base portion 148 may include a plurality of guide and alignment bores 168 near or about a peripheral edge 170. A wire guide or rod 56 is inserted into each of the guide and alignment bores 168 and the corresponding guide and alignment bores 79 provided in the head 36 of the bone plate 22. This allows the head 22 of the targeting arm 81 and the base portion 148 to align with the head 36 of the bone plate 22, as clearly shown in FIGS. 1 and 13.

During insertion and attachment of the bone plate 22 to a patient, an operating physician attaches the targeting device 24 to the bone plate 22. The targeting device 24 of the present invention has several functions. One such function is to insert the bone plate 22 into position along the bone 30. The second feature or function is to align the attachment screws 28 with the screw holes 64 on the bone plate 22 to permit attachment of the bone plate 22 to the bone 30. Another function of the targeting device 24 is to align a syringe (not shown) or other suitable device, which may have a single lumen or multiple lumens, with each access hole or port provided in the top surface of the bone plate 22 for delivering the eluting material to the bone plate 22.

The physician makes a little incision in the patient and, with the targeting device 24, inserts the distal tip of the bone plate 22 into the incision. The bone plate 22 is then slipped beneath the patient's skin and along the bone 30 to its desired position relative to the bone 30. The bone plate 22 is then attached to the bone 30. In one embodiment, the attachment process for each bone screw 28 includes making an incision in the skin above the respective screw hole in the bone plate 22. For example, the incision can be made by means of a scalpel or a very sharp trocar 172 introduced through an outer sleeve member 174 that has been threaded into the appropriate threaded bore of the targeting arm 81 of the targeting device 24. Thereafter, the trocar 172 is removed from the targeting device 24 and replaced with a drill bit 176, introducing the drill bit 176 through the incision, and rotating the drill bit 176 to make a pilot hole in the bone 30. The drill bit 176 is then removed, and the appropriate bone screw is delivered through the outer sleeve 174 and threaded into the screw hole of the bone plate 22 and into the pilot hole in the bone 30 beneath the screw hole of the bone plate 22.

When the eluting material 74 is delivered to the bone plate 22 after insertion and attachment of the bone plate 22, the ports 78 in the outer surface 48 of the bone plate 22 for delivering the material are accessed in one of a plurality of procedures. The first way is via CR or fluoroscopy, for example, live fluoroscopy and a needle. The needle can be of any suitable size ranging from 0.5 to 5.0 millimeters and may be circular, oval or any shape that can accommodate one or more lumens within the syringe. Each access portal or port 78 has a diameter and shape that is slightly larger than the needle to accommodate insertion of the needle therein. In one embodiment, each access port 78 has a diameter of approximately two millimeters. The needle preferably has a diameter that is slightly less than two millimeters to fit into the access port. The needle can be coupled to any suitable reservoir of material, for example, a syringe. Since both the needle and the bone plate 22 can be visualized by fluoroscopy, the needle can be lined up with the respective access port and then inserted through the skin and into the access port during the injection or loading procedure. The material 74 is then injected through the access port 78 into the respective recess 72 provided on the underside of the bone plate 22 by means of the needle.

The second way for delivering the eluting material to the bone plate 22 is by using the targeting device 24 as a guide for lining up the needle with each of the access ports 78 in the bone plate 22. More specifically, the plurality of guide holes 128 in the targeting arm 81 of the targeting device 24 are used to align one or more needles with the respectively aligned access ports 78 extending through the outer surface 48 of the bone plate 22. The eluting material 74 is then introduced in any suitable manner, such as discussed above, through the access ports 78 and into the recesses 72 provided on the underside or bottom surface 50 of the bone plate 22

The drug-eluting material 74 can include a delivery mechanism of any suitable type such as putty, gel or solid. The material can be introduced into the recess in any suitable manner, for example in the form of a liquid, putty or gel. The material can be formed from one or more materials in the recess 72, for example when being delivered by a single or dual lumen needle or other mechanism, or at the back table before being placed in the recess 72. In one embodiment, one or more materials are mixed together and solidify or become a gel, which hardens after a predetermined period of time, for example, after one to 20 minutes. Such material can be introduced through a needle into the access port 78, and hence into the recess or groove 72 provided on the underside of the bone plate 22. As the material is hardening in the groove, it is precluded from dispersing out of the recess 72 by the abutment of the bone plate 22 with the bone 30 or by the biofilm that may be placed over the opening of the groove or other recess 72 at lower surface 50 of the plate 22. Hence, the recess 72 preferably becomes a closed cavity by abutment with the bone 30, the biofilm or both.

One or a plurality of materials can be placed in the recesses 72 of the bone plate 22. Preferably, such materials readily dissolve or elute some medications over a period of time. Such medications can include compounds, proteins or chemicals. The delivery medium or mechanism can be of any suitable type. In one embodiment, the delivery medium does not dissolve but, because there is fluid in the area, the medium elutes whatever is in it. One example of a nondissolving material is bone cement, which is polymethylmethacrilate (PMMA), which is porous. Any medication or material included in such a medium will elute over a certain period of time. In another embodiment, a biodegradable or dissolvable material can be used for the delivery medium. One example of such a dissolving material is calcium sulfate. The eluting material may include medicine or therapeutic agents in a dissolvable material that elutes as the medium dissolves. In another example, the material, which is impregnated with a medication, may, due to an enzyme coupled process, be reduced in size and elute the medications accordingly—much like a bar of soap that reduces in size when used.

It should be understood that the medication or therapeutic agents suitable for time release may include antibiotic compositions, analgesics, bone morphogenic proteins and any other compositions effective for reducing infection and/or promoting healing of a wound found at a surgical site or a fracture. More specifically, a variety of antibiotic drugs can be used in the eluting material to treat or prevent infection. Suitable antibiotics include many classes, such as aminoglycosides, penicillin, semi-synthetic penicillin, cephalosporin, doxycycline, gentamicin, bacitracin, vancomycin, methicillinc, cefazolin, and quinolines. The eluting material may also include antiflammatory agents such as hydrocortisone, prednisone, and the like. Also, the eluting material may include substances useful for promoting growth and survival of cells and tissues or augmenting the functioning of cells. For example, the eluting material may include a nerve growth promoting substance such as a ganglioside, a nerve growth factor, or a hard tissue growth promoting agent such as an osteoinductive growth factor. The eluting material may also include iron or proteins, such as lactoferrin.

In yet a further embodiment, a delivery medium or mechanism can be provided which chemically binds to the medication or other material included therein. One example of such a delivery medium is collagen, which can chemically bind to the medication included therein. For example, bone morphogenic protein (BMP), which is a growth factor of the bone, can combine or attach to a collagen carrier. The BMP or other material bound to the delivery medium is released over a certain period of time because of the binding properties. Any number of other materials can be included in the putty or other delivery mechanism.

As discussed above, the eluting material 74 can be placed in the recesses 72 on the underside of the bone plate 22 before delivery of the bone plate 22 to the patient. For example, the eluting material 74 can be placed manually in the recesses 72 of the bone plate 22 on the back table in the operating room.

The bone plate of the present invention advantageously delivers a medication to the bone without the need for making a large incision in the patient, such as near the bone, for accessing the whole fracture site. Instead, the bone plate can be delivered percutaneously with only a small incision. Large incisions undesirably devascularize the fracture and can thus decrease the ability of the bone to heal and increase the possibility of infection. Longer healing time can result in increased risk of mechanical failure of the bone-fastening device and the need for more operative interventions.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. An implantable bone plate for use with a plurality of attachment screws to treat a portion of an exterior of a bone in a mammalian body comprising an elongate body extending along a longitudinal axis and having substantially parallel outer and inner surfaces, a plurality of holes spaced longitudinally along the elongate body and extending between the outer and inner surfaces adapted to receive the plurality of attachment screws, the inner surface of the elongate body being adapted to overlie the portion of the exterior of the bone and being provided with at least one recess free of the plurality of attachment screws for receiving an eluting material that is delivered to the portion of the exterior of the bone to treat the mammalian body after implantation of the elongate body in the mammalian body, the elongate body being provided with at least one access port extending through the outer surface to the at least one recess for permitting introduction of the eluting material into the at least one recess, the at least one recess having a cross-sectional area at the inner surface and the at least one port having a cross-sectional area at the outer surface less than the cross-sectional area of the recess for inhibiting the escape of eluting material at the outer surface from the at least one recess.

2. The bone plate of claim 1 wherein the at least one recess includes a plurality of recesses spaced longitudinally along the inner surface.

3. The bone plate of claim 2 wherein each of the plurality of recesses is a longitudinal groove.

4. The bone plate of claim 2 wherein each of the plurality of recesses is longitudinally spaced between adjacent holes.

5. A method for preparing a bone plate having an outer surface and an opposite inner surface for engaging a bone of a mammalian body and at least one recess provided in the inner surface comprising extending a biofilm over the at least one recess and introducing an eluting material into the recess so that the eluting material can treat the bone when the bone plate is in the mammalian body.

6. The method of claim 5 wherein the introducing step includes introducing the eluting material through the outer surface into the at least one recess.

7. The method of claim 6 wherein the elongate body is provided with at least one access hole extending through the outer surface and communicating with the at least one recess.

8. A method of treating a mammalian body comprising providing a bone plate having substantially parallel outer and inner surfaces and a plurality of holes extending between the outer and inner surfaces for receiving respective attachment screws and at least one recess distinct from the plurality of holes provided in the inner surface, inserting the bone plate into the mammalian body and introducing an eluting material into the at least one recess when the bone plate is in the mammalian body.

9. The method of claim 8 wherein the introducing step includes introducing the eluting material through the outer surface into the at least one recess.

10. The method of claim 9 wherein the elongate body is provided with at least one access hole extending through the outer surface and communicating with the at least one recess.

11. An apparatus for use with an eluting material and a longitudinally-extending bone plate having opposite outer and inner surfaces and a plurality of longitudinally spaced apart holes aligned in a first pattern for receiving respective attachment screws and a plurality of access ports aligned in a second pattern on the outer surface and communicating with a plurality of recesses provided on the inner surface comprising an elongate body coupleable to the bone plate in a position spaced apart from and extending substantially parallel to the bone plate, the elongate body having a plurality of alignment bores aligned in a pattern corresponding to the first pattern of holes on the bone plate for guiding the attachment screws into the holes of the bone plate and having a plurality of guide holes aligned in a pattern corresponding to the second pattern of access ports on the bone plate, and a tubular needle slideably disposed in at least one guide hole and respective access port for introducing the eluting material through the access port into the respective recess of the bone plate after implantation of the bone plate in a mammalian body.

12. The apparatus of claim 11 wherein the elongate body includes a plurality of longitudinally spaced apart alignment bores alignable with the plurality of longitudinally spaced apart holes in the bone plate for facilitating placement of the attachment screws into the holes of the bone plate.

\* \* \* \* \*